(12) United States Patent
Gregory et al.

(10) Patent No.: US 9,097,708 B2
(45) Date of Patent: Aug. 4, 2015

(54) HIGH-THROUGHPUT METHODOLOGY FOR IDENTIFYING RNA-PROTEIN INTERACTIONS TRANSCRIPTOME-WIDE

(71) Applicant: The Trustees of the University of Pennsylvania, Philadelphia, PA (US)

(72) Inventors: Brian D. Gregory, Swedesboro, NJ (US); John Rinn, Boston, MA (US); Fan Li, Philadelphia, PA (US); Cole Trapnell, Boston, MA (US); Loyal A. Goff, Braintree, MA (US)

(73) Assignee: THE TRUSTEES OF THE UNIVERSITY OF PENNSYLVANIA, Philadelphia, PA (US)

( * ) Notice: Subject to any disclaimer, the term of this patent is extended or adjusted under 35 U.S.C. 154(b) by 0 days.

(21) Appl. No.: 13/911,429

(22) Filed: Jun. 6, 2013

(65) Prior Publication Data

US 2013/0338009 A1    Dec. 19, 2013

Related U.S. Application Data

(60) Provisional application No. 61/656,362, filed on Jun. 6, 2012.

(51) Int. Cl.
| | |
|---|---|
| *C12Q 1/68* | (2006.01) |
| *G01N 33/53* | (2006.01) |
| *C40B 20/00* | (2006.01) |
| *G06F 19/12* | (2011.01) |
| *G06F 19/16* | (2011.01) |

(52) U.S. Cl.
CPC .......... *G01N 33/5308* (2013.01); *C12Q 1/6806* (2013.01); *G06F 19/12* (2013.01); *G06F 19/16* (2013.01)

(58) Field of Classification Search
CPC ... G01N 33/5308; C12Q 1/6806; C40B 20/00
USPC ............................................... 506/2; 435/6.1
See application file for complete search history.

(56) References Cited

U.S. PATENT DOCUMENTS

2005/0227251 A1* 10/2005 Darnell et al. .................... 435/6

OTHER PUBLICATIONS

Hafner et al., "Transcriptome-wide Identification of RNA-Binding Protein and MicroRNA Target Sites by PAR-CLIP," Cell 2010, 141:129-141.*
Roldan et al., "Structural changes in the SL5 and SL6 leader sequences of HIV-1 RNA following interactions with the viral mGag protein," Virus Research 2011, 155:98-105.*
Bailey et al., "MEME SUITE: tools for motif discovery and searching," Nucleic Acids Res. 2009, 37:W202-W208.*
de Silanes et al., "Identification of a target RNA motif for RNA-binding protein HuR," PNAS 2004, 101:2987-2992.*
Cooper, et al., "RNA and Disease", *Cell*, 136(4):777-793 (2009).
Dreyfuss, et al., "hnRNP Proteins and the Biogenesis of mRNA", *Annual Review of Biochemistry*, 62:289-321 (1993).

(Continued)

*Primary Examiner* — Samuel Woolwine
*Assistant Examiner* — Kaijiang Zhang
(74) *Attorney, Agent, or Firm* — Baker Botts L.L.P.

(57) ABSTRACT

Methods of identifying RNA-protein interaction sites are provided. Systems for identifying RNA-protein interaction sites are provided. Systems for identifying secondary structures are provided. Methods of identifying secondary structures are provided. Methods of identifying RNA-binding proteins are provided.

7 Claims, 11 Drawing Sheets

(56) References Cited

OTHER PUBLICATIONS

Glisovic, et al., "RNA-binding proteins and post-transcriptional gene regulation", *FEBS Lett.*, 582(14):1977-1986 (2008).

Keene, "Ribonucleoprotein infrastructure regulating the flow of genetic information between the genome and the proteome", *PNAS*, 98(13):7018-7024 (2001).

Lebedeva, et al., "Transcriptome-wide analysis of regulatory interactions of the RNA-binding protein HuR", *Molecular Cell*, 43(3):340-352 (2011).

Li, et al., "Global analysis of RNA secondary structure in two metazoans", *Cell Press*, 1(1):69-82 (2012).

Lukong, et al., "RNA-binding proteins in human genetic disease", *Trends Genetics*, 24(8):416-425 (2008).

Mukherjee, et al., "Integrative regulatory mapping indicates that the RNA-binding protein HuR couples pre-mRNA processing and mRNA stability", *Molecular Cell*, 43(3):327-339 (2011).

Wang, et al., "Splicing in disease: disruption of the cplicing code and the decoding machinery", *Nature Reviews Genetics*, 8:749-461 (2007).

Zheng, et al., "Genome-wide double-strnded RNA sequencing reveals the functional significance of base-paired RNAs in *Arabidopsis*", *PloS Genetics*, 6(9):e1001141 (2010).

* cited by examiner

HIGH-THROUGHPUT METHODOLOGY FOR IDENTIFYING RNA-PROTEIN INTERACTIONS TRANSCRIPTOME-WIDE

CROSS REFERENCE TO RELATED APPLICATION

This application claims the benefit of U.S. Provisional Application No. 61/656,362, filed Jun. 6, 2012, which is incorporated herein by reference as if fully set forth.

The sequence listing that was electronically filed with this application, titled "Sequence Listing," created on Jun. 6, 2013, and having a file size of 1,647 bytes is incorporated by reference herein as if fully set forth.

FIELD

The disclosure herein relates to transcriptome-wide RNA-protein interaction identification.

BACKGROUND

How eukaryotic organisms regulate gene expression is a fundamental question in biology. It is increasingly clear that regulation of mRNA levels and their translation to corresponding proteins reflects highly coordinated, multi-layered processes. Central to all of these post-transcriptional processes, from the initial processing of a transcript in the nucleus to its final translation and decay in the cytoplasm, are a multitude of complex interactions of each transcript with numerous trans-acting RNA binding proteins.

RNA-binding proteins interact with mRNAs to form dynamic multi-component ribonucleoprotein complexes (RNPs). These RNPs constitute the functional forms of mRNAs, and it is only through their proper formation that transcripts are correctly regulated to precisely produce the required amount of protein in a cell. The importance of RNPs to human biology, in particular, has been demonstrated by studies that show mutations disrupting the assembly of RNPs, as well as specific RNP-contained RNAs or proteins can be deleterious to cells, leading to human diseases. For example, defects in the RNA-binding proteins TAR DNA-binding protein 43 (TDP-43) and Fused in sarcoma/Translocated in liposarcoma (FUS/TLS) have been identified in Amyotrophic Lateral Sclerosis (ALS) patients, as have mutations in FMR1 in those affected with Fragile X syndrome, and Tert in Dyskeratosis congenita patients.

The lack of a comprehensive picture of RNP structures in the human transcriptome is not due to a lack of effort, since numerous biochemical, genetic, and computational approaches have been utilized, alone and in combination, to identify and validate RBP interaction sites (RISs) and their interacting RBPs. What has substantially hindered progress in this field is the fact that RIS structures are often short, highly degenerate, and dependent on secondary structures, making definitive mapping difficult by conventional means. Biochemical techniques to identify precise in vivo occupancy of these sequences remains laborious, and the fact that most of the hundreds of predicted RNA binding proteins have no known function, makes it challenging to determine the true prevalence and regulatory importance of most RNA-protein interactions (Lebedeva et al., 2011; Mukheree et al., 2011, which are incorporated by reference as if fully set forth).

Currently utilized methods for identifying RNA-protein interactions involve purification of a specific RNA-binding protein followed by interrogation of RNAs bound thereto using subsequent sequencing or microarray hybridization. These currently employed approaches include RNA immunopurification followed by microarray hybridization (RIP-chip), high-throughput sequencing of RNAs isolated by crosslinking immunoprecipitation followed by high-throughput sequencing (PAR-CLIP), etc. (Lebedeva et al., 2011; Mukherjee et al., 2011, which are incorporated by reference as if fully set forth). Although these approaches have proven useful in characterizing a few RNPs (for examples see Lebedeva et al., 2011; Mukherjee et al., 2011, which are incorporated by reference as if fully set forth), several drawbacks limit their applicability to global studies of RBP-RNA interactions. For instance, the protein of interest must first be identified and have previously characterized ability to bind RNA. Additionally, an antibody targeted to this single protein of interest must be used to purify the RBP and its associated RNAs. Third, because these methods rely on prior characterization of a known protein, they cannot be used with as of yet unidentified alternative RNA binding domains.

The above observations point to a major gap between the significant importance of RNA-RBP interactions in the cell and the difficulty in establishing a comprehensive accounting of these interactions.

SUMMARY

In an aspect, the invention relates to a method of identifying RNA-protein interaction sites. The method includes preparing RNase footprinting and control libraries, identifying candidate protein binding sites within the RNase footprinting library, and identifying sequence level motifs within the candidate protein binding sites.

In an aspect, the invention relates to a system for identifying RNA-protein interaction sites. The system includes an RNA footprinting database, the RNA footprinting database comprising data associated with an RNA footprinting library, and a processor configured to perform the steps of: identifying candidate protein binding sites within the RNase footprinting library, and identifying sequence level motifs within the candidate protein binding sites.

In an aspect, the invention relates to a system for identifying RNA-protein interaction sites. The system includes one or more processors configured to execute program instructions, and a computer-readable medium containing executable instructions that when executed by the one or more processors, cause the system to perform the steps of: accessing an RNase footprinting library, identifying candidate protein binding sites within the RNase footprinting library, and identifying sequence level motifs within the candidate protein binding sites.

In an aspect, the invention relates to a system for identifying secondary structures. The system includes one or more processors configured to execute program instructions, and a computer-readable medium containing executable instructions that when executed by the one or more processors, cause the computer system to perform the steps of: accessing RNase footprinting and control libraries, and creating secondary structure profiles from the RNase footprinting and control libraries.

In an aspect, the invention relates to a method of identifying secondary structures. The method includes obtaining a first data set comprising ssRNase treated fractions in the presence or absence of bound protein and a second data set comprising dsRNase treated fractions in the presence or absence of bound protein, calculating normalized structure scores from the first data set and the second data set, and creating a secondary structure model from the normalized structure scores.

In an aspect, the invention relates to a method of identifying RNA-binding proteins. The method includes identifying sequence level motifs, preparing an RNA substrate having an identified sequence level motif, exposing the RNA substrate to a sample containing candidate RNA-binding proteins, and isolating candidate RNA binding proteins interacting with the RNA substrate. An isolated candidate RNA binding protein interacting with the RNA substrate is identified as one of the RNA binding proteins.

In an aspect, the invention relates to an isolated nucleic acid molecule comprising a sequence having at least 87.5% identity to one selected from the group consisting of Motif 5-AGAAGGCA, Motif 26-TGGTTAGTACTT [SEQ ID NO: 1], Motif 4-ATCTGATC, Motif 7-GATCTCGGAAG [SEQ ID NO: 2], Motif_UTR_4-GAAGCTAAGC [SEQ ID NO: 3], 3' UTR C-rich element-GCCCCCTCCCCCCCCCCCCC [SEQ ID NO: 4], 3' UTR Unknown element-AGCAGAAG, 3' UTR Unknown hairpin-CAGGCCGTGCTGCTGCCCA [SEQ ID NO: 5], 5' UTR GGC repeat-GGCGGCGGCG-GCGGC [SEQ ID NO: 6], 5' UTR CAG repeat-CGGCAG-CAGCAGCAGAAG [SEQ ID NO: 7], 3' UTR TG repeat-TGTGTGTGTGTGTGTGTGTG [SEQ ID NO: 8] 5' UTR Unknown element-AAGATGGCGGC [SEQ ID NO: 9], CDS AAG repeat-AGAAGAAG, and Intronic Unknown element-CTGTAGAA.

BRIEF DESCRIPTION OF THE DRAWINGS

The following detailed description of the preferred embodiments of the present invention will be better understood when read in conjunction with the appended drawings. For the purpose of illustrating the invention, there are shown in the drawings embodiments which are presently preferred. It is understood, however, that the invention is not limited to the precise arrangements and instrumentalities shown. In the drawings.

DETAILED DESCRIPTION OF THE PREFERRED EMBODIMENTS

Figure 1A:
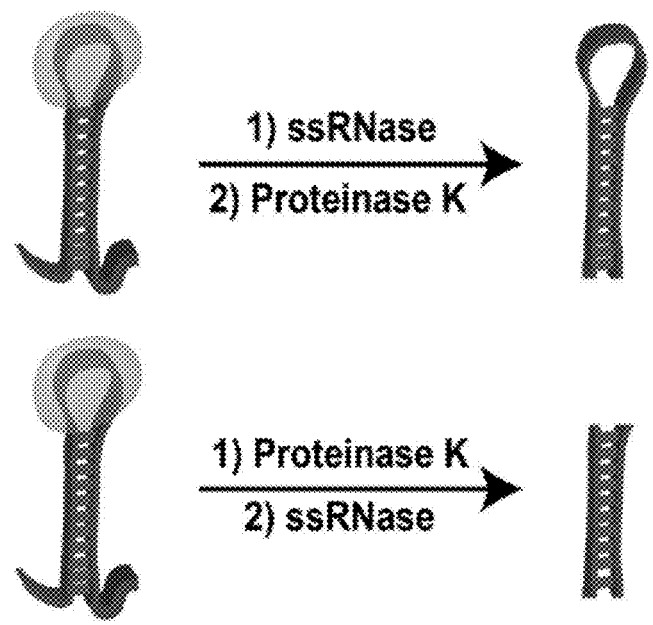
FIGS. 1A-1C illustrate RNase footprinting assays.

Certain terminology is used in the following description for convenience only and is not limiting. The words "right," "left," "top," and "bottom" designate directions in the drawings to which reference is made. The words "a" and "one," as used in the claims and in the corresponding portions of the specification, are defined as including one or more of the referenced item unless specifically stated otherwise. This terminology includes the words above specifically mentioned, derivatives thereof, and words of similar import. The phrase "at least one" followed by a list of two or more items, such as "A, B, or C," means any individual one of A, B or C as well as any combination thereof.

To advance the understanding of eukaryotic gene expression regulation, it is necessary to globally identify and investigate RNA binding proteins (RBPs) and their binding sites within RNA molecules at a transcriptome-wide level. The precise composition and formation of RNPs in eukaryotic cells is a critical node for proper gene expression regulation. Although it is apparent that RNPs are important for eukaryotic biology, a comprehensive analysis of the composition of these RNA-protein complexes has never been performed for any organism.

Figure 1B:
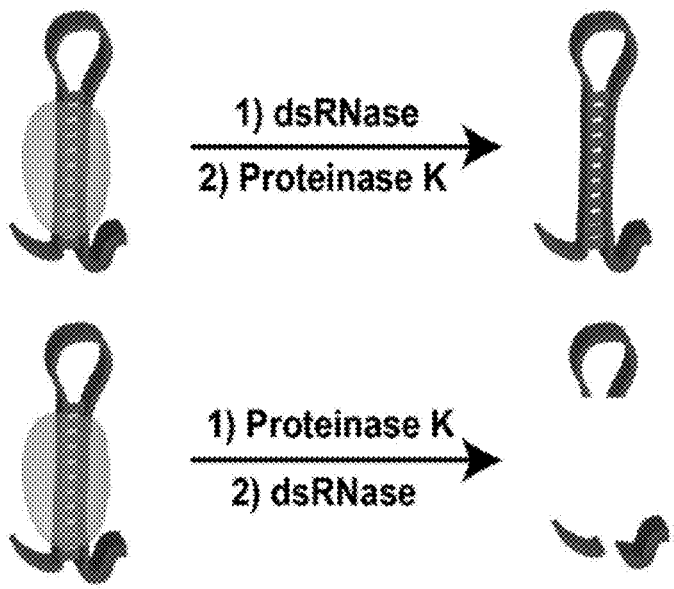
Figure 1C:
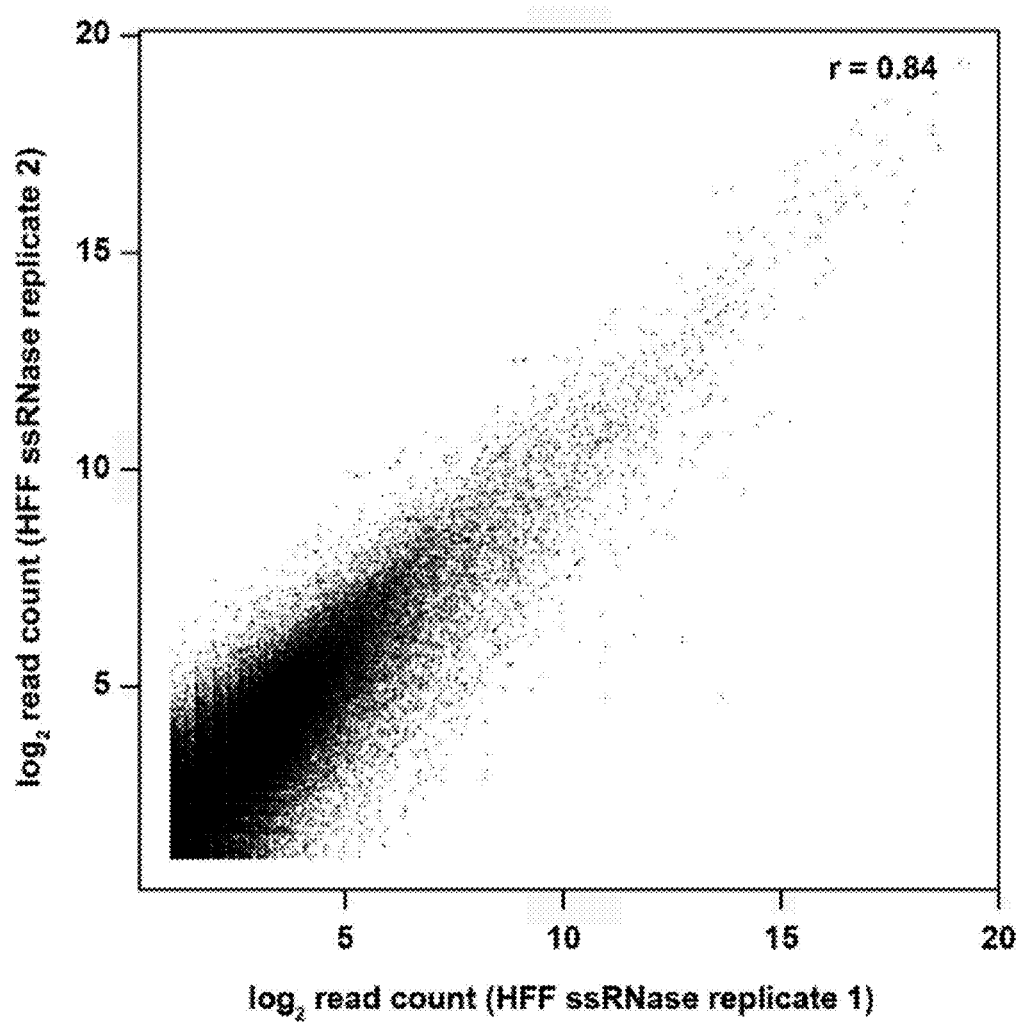

An approach was developed that allows the identification of RNA-protein interactions on a transcriptome-wide scale. To do this, the recently reported nuclease-based, high-throughput sequencing approach (Li et al., 2012; Zheng et al., 2010, which are incorporated by reference as if fully set forth) was modified. By performing the innovative, transcriptome-wide, nuclease-sensitivity assays on RNAs crosslinked with their interacting proteins, all sites of RNA-protein interaction within a transcriptome of interest can be determined. Specifically, through identification of the RNA regions that are resistant to RNases (ss- and dsRNases) in the presence, but not the absence of bound proteins, the sites of protein-RNA interactions can be uncovered (FIGS. 1A-1C). In total, the data produced by the multi-faceted approach reveal the prevalence of RNA-protein interaction sites throughout a transcriptome of interest. In addition, in the process of validating the findings from this approach, numerous novel RBPs can be identified that have eluded prior studies. Embodiments herein include this approach.

Embodiments herein include methods of determining RNA-protein interaction sites within a transcriptome of interest. Methods of determining RNA-protein interaction sites may include an RNase footprinting approach. An RNase footprinting approach may include preparing an RNase footprinting library, identifying candidate protein binding sites, and identifying sequence-level motifs within the candidate protein binding sites.

A schematic of an RNase footprinting approach in FIGS. 1A-1C shows that a cross-linked RNA-binding protein protects a single-strand loop from digestion by an ssRNase. (FIG. 1A, top). An ssRNase implemented may be but is not limited to RNaseOne. However, if the bound protein is first removed by protease or proteinase digestion (FIG. 1A, bottom), this single-stranded loop is degraded by the ssRNase. A non-limiting example of an enzyme that may be implemented to remove protein is Proteinase K. By comparing the dataset from the top example in FIG. 1A to the bottom, all protein bound regions in unpaired portions of RNAs can be identified. As shown in (FIG. 1B), a dsRNase will degrade the base-paired stem in the absence of a bound protein, but not in its presence. A dsRNase implemented may be but is not limited to RNaseV1. By comparing similar datasets in FIG. 1B (top and bottom) obtained for dsRNase digestion, all protein-bound regions in paired portions of RNAs can be determined.

Preparing the RNase footprinting library. Cells of interest may be cross-linked. Cross-linking may be achieved by any suitable method including but not limited to ultra violet radiation, or formaldehyde treatment. Formaldehyde treatment may include adding 37% formaldehyde drop-wise with mixing directly to culture plates to a final concentration of 1%, and shaking the plates for 10 mins at room temperature (RT). Next, 1M glycine may be added to a final concentration of 125 mM, and the plates may be gently shaken for 5 mins at RT. Then the cells may be washed and collected in PBS. UV crosslinking may include placing a dish of cells in a Pyrex dish filled with ice (the ice may create a flat surface), removing the top of the dish, and crosslinking with 0.4 uJ using a UV crosslinker or some other UV source. Then the cells may be washed and collected in PBS. Cells prepared by any cross-linking method may be pelleted and can be frozen or used directly in the assay. Cell pellets from any cross-linking method may be formed by pooling plates of cells. For example, five plates of cells may be pooled to make each cell pellet to sample biological and technical diversity between the different plates of cells.

Preparing the RNase footprinting library may include obtaining a sample from the cell of interest. Obtaining the sample may include lysing the cell of interest to obtain the sample. The sample may be treated with DNase.

Preparing the RNase footprinting library may include lysing the cross-linked cell pellets using any suitable reagent. This may include any type of lysis buffer. For example, the cross-linked cell pellets may be lysed using RIP buffer (25 mM Tris-HCL, pH=7.4; 150 mM KCl, 5 mM EDTA, pH=7.5; 0.5% NP40; 10 µM DTT; 1 tablet protease inhibitors/10 mL) and manual grinding. The lysed samples may be treated with RNase-free DNase. A non-limiting example of such a DNase is RNase-free DNase from Qiagen; Valencia, Calif. Subsequently, the DNA-depleted fractions may be treated with either a single-stranded RNase (ssRNase) or double-stranded RNase (dsRNase) as previously described ((Li t al., 2012; Zheng et al., 2010, which are incorporated by reference as if fully set forth). A non-limiting example of an ssRNase is RNaseONE (Promega; Madison, Wis.). A non-limiting example of dsRNase is RNaseV1 (Ambion; Austin, Tex.). See FIGS. 1A-1C for a schematic description. Proteins may be digested by treatment with protease or proteinase (e.g. Proteinase K (Roche; Basel, Switzerland)). There may be two cell lysates for these experiments: one treated with the ssRNase and the other with dsRNase. RNase digestion may be followed by cross-link reversal. Cross-link reversal may be done through a 2-hour incubation at 65° C. to reverse formaldehyde induced crosslinks. The digested RNA may be isolated using any suitable technique. For example, the Qiagen miRNeasy RNA isolation kit may be implemented to isolate the digested RNA by following the included protocol (Qiagen; Valencia, Calif.). Purified RNA may be used as the substrate for strand-specific sequencing library preparation, as previously described (Li et al., 2012; Zheng et al., 2010). DSN library normalization may also be included per manufacturer instructions (Illumina; San Diego, Calif.).

Preparing the RNase footprinting library may include determining whether nuclease resistant regions in RNAs are due to protein binding or specific secondary structures. This may include determining the digestion patterns of ds- and ssRNases in the absence of bound proteins by producing an RNase footprinting control library. To do this, treatments may be performed as described directly above except that the cross-linked cellular lysates may be treated with protease or proteinase before being treated with an RNase. A protease or proteinase may digest the proteins and allow deduction of protein-protected sites within all detectable RNAs in the cells (FIGS. 1A-1C).

Methods of determining RNA-protein interaction sites may include identifying candidate protein binding sites. Identifying candidate protein binding sites may include a modified ChIP-seq peak calling algorithm. Specifically, normalized read coverages may be calculated for each base position in the genome and a Poisson test may be used to compute an enrichment score for 'protected' versus 'unprotected' libraries. RNA-protein interaction sites, also referred to as protein-protected sites (PPSs), may then be called by searching for regions with an enrichment score that exceeds a computed threshold. This threshold may be determined by randomly shuffling 'RNase footprinting' and 'RNase footprinting control' reads, repeating the enrichment score calculation, and selecting the top 5% of scores that emerge as peaks in the randomized data. In essence, the selected threshold acts to limit the false discovery rate (FDR) of the approach. PPSs from dsRNase-treated and ssRNase-treated samples may then be merged as a comprehensive list of protein-protected sites for that specific experiment. The functional classification of these differentially expressed regions may be determined. Predicted binding sites may be compared with previously published protein data to determine the significance of overlap as described below (see FIGS. 2A-4B).

Motif discovery and experimental validation. Methods of determining RNA-protein interaction sites may include identifying sequence-level motifs within the candidate protein binding sites. Identifying sequence-level motifs within the candidate protein binding sites may include identifying the candidate protein binding found specifically in the 5' UTR, protein-coding region and 3' UTR. These specific sets of protein binding site sequences may then be used to perform a motif search using MEME (available at meme.sdsc.edu/meme/ and described in Timothy L. Bailey, Mikael Bodén, Fabian A. Buske, Martin Frith, Charles E. Grant, Luca Clementi, Jingyuan Ren, Wilfred W. Li, William S. Noble, "MEME SUITE: tools for motif discovery and searching", *Nucleic Acids Research*, 37:W202-W208, 2009, which is incorporated herein by reference as if fully set forth) or other motif finding algorithms. Multiple motifs may be allowed, including but not limited to up to an E-value cutoff of 0.01, within the dataset to fully capture the protein-binding component of the transcriptome. The resulting motifs may be validated by a competitive pulldown assay as described below. See FIGS. 4A-4B for examples of motifs already identified by the initial RNase footprinting experiments in HeLa cells.

Comparison of protein-protected regions (RNase 'footprints') between cell types and fractions. In order to identify shifts/differences in protein binding sites between cell types and/or biological conditions, datasets may be compared in pair-wise analyses (e.g. cell type 1 vs. cell type 2). Specifically, to determine the RNA-protein interaction sites (PPSs) that show significant changes between cell types and/or biological conditions, negative binomial-based differential expression analyses may be applied pairwise (e.g. cell type 1 vs. cell type 2) to pseudo-read counts. These pseudo-read counts may be calculated in a manner to preserve the relative read ratios of (+) protein to (−) protein samples within each cell type/biological condition. Specifically, pseudocounts for each j-th PPS under cell types/conditions a and b may be calculated as:

$$C_j^a = [r_i^{a(+)}/r_i^{a(-)}]*R_i \text{ and } C_j^b = [r_i^{b(+)}/r_i^{b(-)}]*R_i$$

where $r_i^{a(+)}$ are the read coverages from (+) protein samples and $r_i^{a(-)}$ are the read coverages from (−) protein samples of the j-th PPS under condtion a. The ratio $r_i^{a(+)}/r_i^{a(-)}$ is thus a vector (across replicates) of the relationship between (+) and (−) protein read coverage under condition a. $r_i^{b(+)}/r_i^{b(-)}$ is a vector (across replicates) of the relationship between (+) and (−) protein read coverages under condition b, and $R_j$ is the average read coverage across all (−) protein replicates in both conditions. The pseudocount vectors $C_j^a$ and $C_j^b$ may then be directly compared to identify cell type/biological condition-impacted RNA-protein interaction sites. In this way, the RBP-RNA interaction sites that are dynamically gained or lost between cell types and/or biological conditions may be comprehensively identified. Then to determine the degree of similarity in RBP-mRNA interaction site architecture between the cell types and/or biological conditions, an indicator variable may be defined based on the identified PPSs:

$X_{ij} = 0$, if $PPS\ i$ in a specific condition $j$ is not significantly protein protected $= 1$, if $PPS\ i$ in a specific condition $j$ is significantly protein protected The distribution of protein-protected regions may then be characterized by examining various combinations of the indicator vectors $X_j$ (e.g. sites present only in cell type 1, only in cell type 2, in both cell types). Next, the pairwise Euclidean distances between the $X_j$ vectors may be calculated and a hierarchical clustering analysis of the various conditions being assayed may be performed.

An embodiment includes methods of identifying RNA binding proteins. Methods of identifying RNA binding proteins may include isolating interacting proteins corresponding to motifs by an affinity pull-down assay.

Identification of novel RBPs as validation of RNase footprinting

The RNase footprinting validation studies may identify novel human RNA binding proteins. The motifs identified using an RNase footprinting approach (FIGS. 4A-4B) are protected from RNase digestion by a bound protein (see FIGS. 1A-1C for example). Therefore, the motifs may be used as baits to isolate by affinity "pull-down" studies the corresponding interacting proteins. By using novel motifs (not found in any RBP binding database, identification of novel RBPs is likely.

To do this, the cells of interest, may be grown as specified above. When the cells reach 80-90% confluence, total cell lysates may be prepared. For example, total cell lysates may be prepared by adding 500 μl of lysis buffer (20 mM HEPES pH 7.9, 1% Triton X-100, 100 mM KCl, 2.2 mM MgCl$_2$ 1 mM DTT, 10% glycerol, 0.1 mM PMSF, and a Protease inhibitor cocktail tablet/10 mL). Total cell lysates may be lightly sonicated and centrifuged, for example, for 10 mins at 16000 g, 4° C. Supernatants may then be transferred to a new tube and quantified. Quantification may include measuring absorbance at 280 nm. Egg white avidin (EMD chemicals 10 μg/mg protein) and yeast tRNA (Sigma, 0.5 mg/mg protein) may be added to the cell lysates to block endogenous biotinylated proteins and non-specific RBPs, and may be incubated on a rotatory shaker at 4° C. for 20 mins. After blocking, lysates may be centrifuged, for example for 10 mins at 16000 g, 4° C. Supernatants may then be transferred to new tubes and RNasin may be added (Promega, 200 U/ml).

RNA substrates may be made for identification of RBPs that interact with a specific RNA motif. The RNA substrates may include a tag used to isolate or immobilize the RNA. The tag may be a biotin moiety. Making the RNA substrates for identification of the RBP that interacts with a specific RNA motif (see FIGS. 4A-4C for examples of identified motifs) may include immobilizing 3' biotinylated RNA probes (Dharmacon) on streptavidin-coated magnetic beads (Invitrogen) as per manufacturer's instructions. For example, biotinylated RNA sequences containing a candidate protein binding motif and flanking linker regions may be used to identify the proteins that bind specifically to the motif of interest. An array of negative controls may be produced where 3' biotinylated RNA probes with the same nucleotide composition as the candidate motif but with different sequences may be attached to magnetic beads (scrambled controls). The RNA-coated beads may then be equilibrated by washing twice with binding buffer (a non-limiting binding buffer example may include 20 mM HEPES-KOH pH 7.9, cocktail tablet) and may be resuspended in binding buffer, for example, 500 μl of binding buffer.

A protein pull-down may include binding tagged RNAs to samples and recovering bound proteins via the tag. A non-limiting example of a protein pull-down may be performed as follows: 500 μl of total cell extract produced as described above may be added to RNA-coated beads, and these samples may be incubated with end-over-end rotation, for example, for 30 mins at 4° C., and then for an additional 30 mins at room temperature. The magnetic beads may then be separated from bulk liquid with a 12 tube magnetic rack (Ambion) and the supernatant may be removed. Beads may then be washed twice, for example, with 100 μl of Wash buffer (a non-limiting example may include binding buffer containing 150 mM KCl), twice with 100 μl of elution buffer (a non-limiting example may include binding buffer with 750 mM KCl), and twice with EB' buffer (a non-limiting example may include binding buffer with 1.5M KCl). All supernatants may be collected and used for downstream analysis. To ensure that all bound proteins are removed from the RNA substrates, the RNA-coated beads may be boiled in 100 μl of gel loading buffer containing SDS (Invitrogen). To begin analysis of purified proteins, half of each sample may be analyzed by SDS-PAGE and the other half may be used directly for mass spectrometry (MS) analyses.

Figure 5:
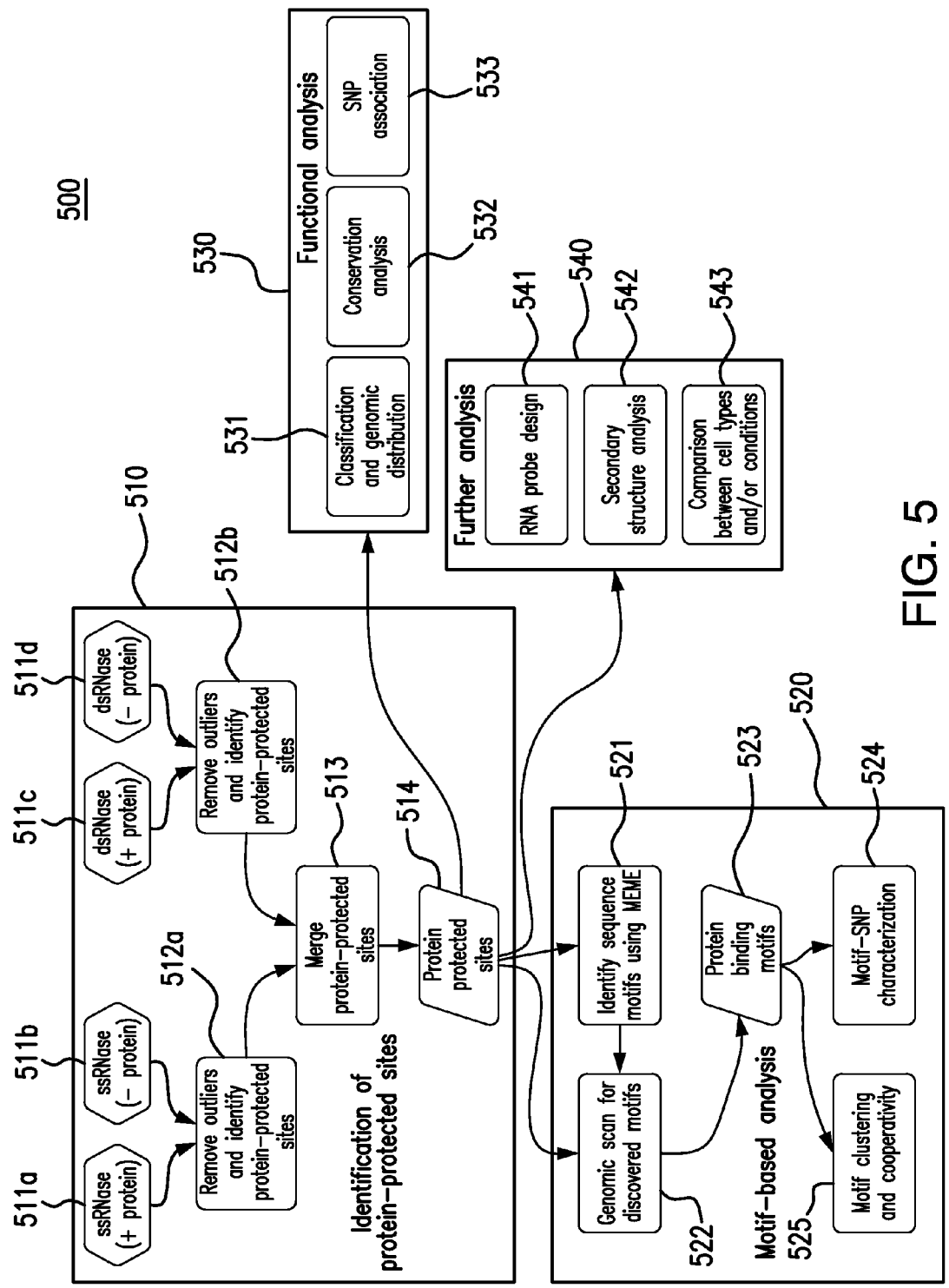
FIG. 5 illustrates an RNase footprinting workflow diagram.

Embodiments include computational pipelines for executing an RNase footprinting workflow. Computational pipelines for executing an RNase footprinting workflow may include methods of determining RNA-protein interaction sites using an RNase footprinting approach. Referring to FIG. 5, a computational pipeline executing an RNase footprinting workflow 500 is illustrated with steps including identification of protein-protected sites 510, motif-based analysis 520, functional analysis 530 and further analysis 540. Identification of protein-protected sites 510 may include acquiring an RNase footprinting assay data set from ssRNase treated fractions in the presence of bound protein 511a, ssRNase treated fractions in the absence of bound protein 511b, dsRNase treated fractions in the presence of bound protein 511c and dsRNase treated fractions in the absence of bound protein 511d; removing outliers and identifying protein-protected sites from each ssRNase treated fraction 512a and removing outliers outliers and identifying protein-protected sites from each dsRNase treated fraction 512b; merging the identified protein-protected sites from each fraction 513; and identifying final protein protected sites 514. Motif-based analysis 520 may include identifying sequence motifs using MEME 521 (or other algorithms for finding over-represented sequence motifs), genomic scanning for discovered motifs 522, identifying protein binding motifs 523, characterizing motif-SNP interactions 524 and assessing motif clustering and cooperativity 525. Functional analysis 530 may include classifying protein-protected sites and determining their genomic distribution 531, analyzing protein-protected site conservation 532 and determining protein-protected site SNP association 533. Further analysis 540 may include designing RNA probes 541, identifying secondary structure causing RNase resistance 542, and comparing results between different cell types or different biological conditions 543. The different cell types may be but are not limited to being from different sources in a species or may be from different species. The different biological conditions may be but are not limited to being from different developmental stages of a species, different pathologic states, or different ages.

Embodiments may include a computer system for identifying RNA-protein interaction sites comprising one or more processors configured to execute program instructions and a computer-readable medium containing executable instructions that, when executed by the one or more processors, cause the computer system to perform a method of identifying RNA-protein interaction sites comprising one or more steps from the computational pipeline executing an RNase footprinting workflow.

Embodiments may include a computer program product, comprising a tangible computer readable medium comprising executable instructions for affecting one or more steps from the computational pipeline executing an RNase footprinting workflow.

Figure 6:
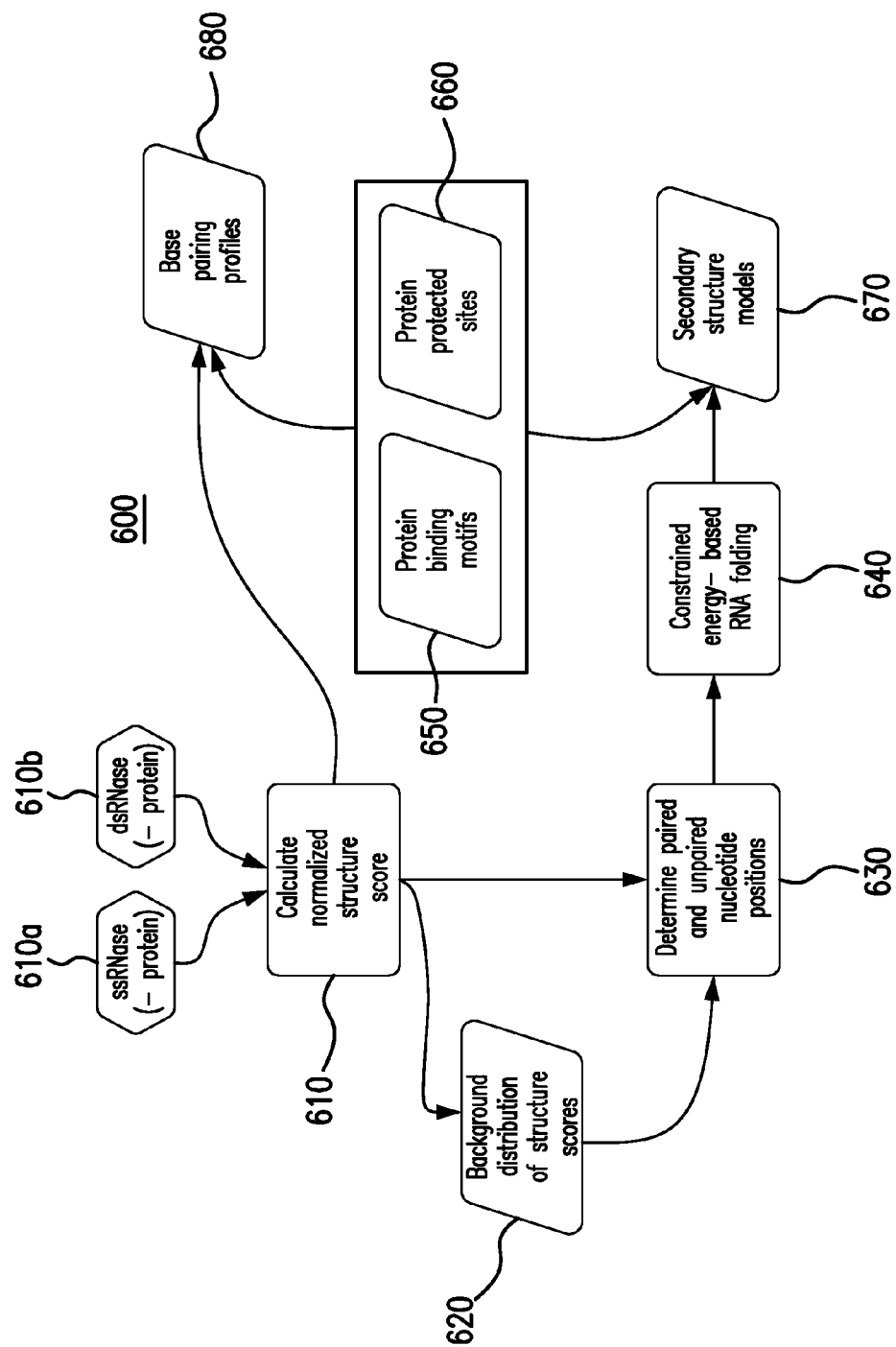
FIG. 6 illustrates a secondary structure workflow diagram.

Embodiments include computational pipelines for executing a secondary structure workflow. Referring to FIG. 6, a computational pipeline executing a secondary structure workflow 600 is illustrated. The computation pipeline may include calculating normalized structure scores 610 from ssRNase treated fractions 610*a* and dsRNase treated fractions 610*b* in the absence of bound protein, determining a background distribution of structure scores 620, determining paired and unpaired nucleotide positions 630, determining constrained free energy-based RNA folding 640, identifying protein binding motifs 650, identifying protein protected sites 660, creating base pairing profiles 670 and creating secondary structure models 680.

Embodiments may include a computer system for identifying RNA secondary structures comprising one or more processors configured to execute program instructions and a computer-readable medium containing executable instructions that, when executed by the one or more processors, cause the computer system to perform a method of identifying RNA secondary structures comprising one or more steps from the computational pipeline executing a secondary structure workflow.

Embodiments may include a computer program product, comprising a tangible computer readable medium comprising executable instructions for affecting one or more steps from the computational pipeline executing a secondary structure workflow.

Embodiments may include sequence level motifs in protein binding sites. An embodiment provides an isolated nucleotide sequence having at least 70, 72, 75, 80, 85, 87.5, 90, 91, 92, 93, 94, 95, 96, 97, 98, 99, or 100% identity to a motif sequence selected from the group consisting of Motif 5-AGAAGGCA, Motif 26-TGGTTAGTACTT [SEQ ID NO: 1], Motif 4-ATCTGATC, Motif 7-GATCTCGGAAG [SEQ ID NO: 2], Motif_UTR_4-GAAGCTAAGC [SEQ ID NO: 3], 3' UTR C-rich element-GCCCCCTCCCCCCCCCCCCC [SEQ ID NO: 4], 3' UTR Unknown element-AGCAGAAG, 3' UTR Unknown hairpin-CAGGCCGTGCTGCTGCCCA [SEQ ID NO: 5], 5' UTR GGC repeat-GGCGGCGGCGGCGGC [SEQ ID NO: 6], 5' UTR CAG repeat-CGGCAGCAGCAGCAGAAG [SEQ ID NO: 7], 3' UTR TG repeat-TGTGTGTGTGTGTGTGTG [SEQ ID NO: 8], 5' UTR Unknown element-AAGATGGCGGC [SEQ ID NO: 9], CDS AAG repeat-AGAAGAAG, and Intronic Unknown element-CTGTAGAA.

The isolated nucleotide sequence may be implemented in a method herein. Determining percent identity of two nucleic acid sequences may include aligning and comparing the amino acid residues or nucleotides at corresponding positions in the two sequences. If all positions in two sequences are occupied by identical amino acid residues or nucleotides then the sequences are said to be 100% identical. Percent identity may be measured by the Smith Waterman algorithm (Smith T F, Waterman M S 1981 "Identification of Common Molecular Subsequences," J Mol Biol 147: 195-197, which is incorporated herein by reference as if fully set forth).

A computing device may be used to implement features described herein with reference to FIGS. 5-6. An example computing device may include a processor, memory device, communication interface, peripheral device interface, display device interface, and data storage device. A display device may be coupled to or included within the computing device.

The memory device may be or include a device such as a Dynamic Random Access Memory (D-RAM), Static RAM (S-RAM), or other RAM or a flash memory. The data storage device may be or include a hard disk, a magneto-optical medium, an optical medium such as a CD-ROM, a digital versatile disk (DVDs), or Blu-Ray disc (BD), or other type of device for electronic data storage.

The communication interface may be, for example, a communications port, a wired transceiver, a wireless transceiver, and/or a network card. The communication interface may be capable of communicating using technologies such as Ethernet, fiber optics, microwave, xDSL (Digital Subscriber Line), Wireless Local Area Network (WLAN) technology, wireless cellular technology, and/or any other appropriate technology.

The peripheral device interface is configured to communicate with one or more peripheral devices. The peripheral device interface operates using a technology such as Universal Serial Bus (USB), PS/2, Bluetooth, infrared, serial port, parallel port, and/or other appropriate technology. The peripheral device interface may, for example, receive input data from an input device such as a keyboard, a mouse, a trackball, a touch screen, a touch pad, a stylus pad, and/or other device. Alternatively or additionally, the peripheral device interface may communicate output data to a printer that is attached to the computing device via the peripheral device interface.

The display device interface may be an interface configured to communicate data to display device. The display device may be, for example, a monitor or television display, a plasma display, a liquid crystal display (LCD), and/or a display based on a technology such as front or rear projection, light emitting diodes (LEDs), organic light-emitting diodes (OLEDs), or Digital Light Processing (DLP). The display device interface may operate using technology such as Video Graphics Array (VGA), Super VGA (S-VGA), Digital Visual Interface (DVI), High-Definition Multimedia Interface (HDMI), or other appropriate technology. The display device interface may communicate display data from the processor to the display device for display by the display device. The display device may be external to the computing device, and coupled to the computing device via the display device interface. Alternatively, the display device may be included in the computing device.

An instance of the computing device may be configured to perform any feature or any combination of features described above as performed by the client device. Alternatively or additionally, the memory device and/or the data storage device may store instructions which, when executed by the processor, cause the processor to perform any feature or any combination of features described above. Alternatively or additionally, each or any of the features described above may be performed by the processor in conjunction with the memory device, communication interface, peripheral device interface, display device interface, and/or storage device.

A tablet computer is a more specific example of the computing device. The tablet computer may include a processor, memory device, communication interface, peripheral device interface, display device interface, storage device, and touch screen display, which may possess characteristics of the processor, memory device, communication interface, peripheral device interface, display device interface, storage device, and display device, respectively, as described above. The touch screen display may receive user input using technology such as, for example, resistive sensing technology, capacitive sensing technology, optical sensing technology, or any other appropriate touch-sensing technology.

As used herein, the term "processor" broadly refers to and is not limited to a single- or multi-core processor, a special purpose processor, a conventional processor, a Graphics Processing Unit (GPU), a digital signal processor (DSP), a plurality of microprocessors, one or more microprocessors in association with a DSP core, a controller, a microcontroller, one or more Application Specific Integrated Circuits (ASICs), one or more Field Programmable Gate Array (FPGA) circuits, any other type of integrated circuit (IC), a system-on-a-chip (SOC), and/or a state machine.

As used to herein, the term "computer-readable medium" broadly refers to and is not limited to a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVDs, or BD, or other type of device for electronic data storage.

As used herein, the term "processor" broadly refers to and is not limited to a single- or multi-core central processing unit (CPU), a special purpose processor, a conventional processor, a Graphics Processing Unit (GPU), a digital signal processor (DSP), a plurality of microprocessors, one or more microprocessors in association with a DSP core, a controller, a microcontroller, one or more Application Specific Integrated Circuits (ASICs), one or more Field Programmable Gate Array (FPGA) circuits, any other type of integrated circuit (IC), a system-on-a-chip (SOC), and/or a state machine.

As used to herein, the term "computer-readable medium" broadly refers to and is not limited to a register, a cache memory, a ROM, a semiconductor memory device (such as a D-RAM, S-RAM, or other RAM), a magnetic medium such as a flash memory, a hard disk, a magneto-optical medium, an optical medium such as a CD-ROM, a DVD, or BD, or other type of device for electronic data storage.

Although features are described herein as being performed in a computing device, the features described herein may also be implemented, mutatis mutandis, on or in cooperation with a desktop computer, a laptop computer, a netbook, a cellular phone, a personal digital assistant (PDA), or any other appropriate type of tablet computing device or data processing device. The systems and methods described herein may be performed on a single computing device or a plurality of computing devices.

Although features and elements are described above in particular combinations, each feature or element can be used alone or in any combination with or without the other features and elements. For example, each feature or element as described above may be used alone without the other features and elements or in various combinations with or without other features and elements. Sub-elements of the methods and features described above may be performed in any arbitrary order (including concurrently), in any combination or sub-combination.

Embodiments

The following list includes particular embodiments. The list, however, is not limiting and does not exclude embodiments otherwise described or alternate embodiments, as would be appreciated by one of ordinary skill in the art.

1. A method of identifying RNA-protein interaction sites comprising:
   preparing RNase footprinting and RNase control libraries;
   identifying candidate protein binding sites within the RNase footprinting library; and
   identifying sequence level motifs within the candidate protein binding sites.

2. The method of embodiment 1, wherein preparing an RNase footprinting libarary includes:
   crosslinking at least one cell;
   obtaining a sample from the at least one cell;
   treating a first fraction of the sample with single-stranded RNase;
   treating a second fraction of the sample with double-stranded RNase;
   treating both the first and the second fractions with protease or proteinase;
   isolating RNA from the first fraction and the second fraction; and
   preparing a strand specific sequence library.

3. The method of embodiment 1, wherein preparing an RNase footprinting control library includes:
   crosslinking at least one cell;
   obtaining a sample from the at least one cell;
   treating a first fraction of the sample with protease or proteinase;
   treating a second fraction of the sample with protease or proteinase;
   treating the first fraction of the sample with single-stranded RNase;
   treating the second fraction of the sample with double-stranded RNase;
   isolating RNA from the first fraction and the second fraction; and
   preparing a strand specific sequence library.

4. The method of any one or more of embodiments 1-3, wherein obtaining the sample includes lysing the at least one cell to obtain the sample.

5. The method of any one or more of embodiments 1-4 further comprising treating the sample with DNase.

6. The method of any one or more of embodiments 1-5 further comprising treating the sample with protease or proteinase after RNase treatment.

7. The method of any one or more of embodiments 1-6 further comprising treating at least one of the first fraction or the second fraction of the sample with protease or proteinase before RNase treatment.

8. The method of any one or more of embodiments 1-7, wherein identifying candidate protein binding sites includes identifying protein protected sites; and comparing the protein protected sites with previously published protein data.

9. The method of any one or more of embodiments 1-8, wherein identifying sequence level motifs includes selecting a site specific candidate protein binding site from the candidate protein binding sites; and performing a MEME motif search on the site specific candidate protein binding site to identify at least one motif.

10. The method of any one or more of embodiments 1-9, wherein the site specific candidate binding site is found in the 5' UTR, the protein coding region, or the 3' UTR.

11. The method of any one or more of embodiments 1-10 further comprising validating the at least one motif by a competitive pull-down assay.

12. A system for identifying RNA-protein interaction sites comprising:

an RNA footprinting database, the RNA footprinting database comprising data associated with an RNA footprinting library; and a processor configured to perform the steps of:

identifying candidate protein binding sites within the RNase footprinting library; and identifying sequence level motifs within the candidate protein binding sites.

13. The system of embodiment 12, wherein the data associated with an RNA footprinting library is obtained by preparing RNase footprinting and control libraries.

14. The system of embodiment 13, wherein preparing an RNase footprinting library includes:

crosslinking at least one cell;

obtaining a sample from the at least one cell;

treating a first fraction of the sample with single-stranded RNase;

treating a second fraction of the sample with double-stranded RNase;

treating both fractions of the sample with a protease or proteinase;

isolating RNA from the first fraction and the second fraction; and preparing a strand specific sequence library.

15. The system of embodiment 13, wherein preparing an RNase footprinting control library includes:

crosslinking at least one cell;

obtaining a sample from the at least one cell;

treating a first fraction of the sample with protease or proteinase;

treating a second fraction of the sample with protease or proteinase;

treating the first fraction of the sample with single-stranded RNase;

treating the second fraction of the sample with double-stranded RNase;

isolating RNA from the first fraction and the second fraction; and preparing a strand specific sequence library.

16. The system of embodiment 13-15, wherein obtaining the sample includes lysing the at least one cell to obtain the sample.

17. The system of any one or more of embodiments 13-16 further comprising treating the sample with DNase.

18. The method of any one or more of embodiments 13-17 further comprising treating the sample with protease or proteinase.

19. The method of any one or more of embodiments 13-17 further comprising treating at least one of the first fraction or the second fraction of the sample with protease or proteinase.

20. The system of any one or more of embodiments 13-19, wherein identifying candidate protein binding sites includes identifying protein protected sites; and comparing the protein protected sites with previously published protein data.

21. The system of any one or more of embodiments 12-20, wherein identifying sequence level motifs includes selecting a site specific candidate protein binding site from the candidate protein binding sites; and performing a MEME motif search on the site specific candidate protein binding site to identify at least one motif.

22. A system for identifying RNA-protein interaction sites comprising:

one or more processors configured to execute program instructions;

a computer-readable medium containing executable instructions that when executed by the one or more processors, cause the system to perform the steps of:

accessing an RNase footprinting library and a control library;

identifying candidate protein binding sites within the RNase footprinting library; and identifying sequence level motifs within the candidate protein binding sites.

23. The system of embodiment 20 further comprising the step of compiling data to obtain the RNase footprinting and the control library.

24. The system of any one or more of embodiments 22-23 wherein the RNase footprinting libarary is prepared by:

crosslinking at least one cell;

obtaining a sample from the at least one cell;

treating a first fraction of the sample with single-stranded RNase;

treating a second fraction of the sample with double-stranded RNase;

treating the first fraction and the second fraction with a protease or proteinase;

isolating RNA from the first fraction and the second fraction; and preparing a strand specific sequence library.

25. The system of any one or more of embodiments 22-24, wherein preparing an RNase footprinting control library includes:

crosslinking at least one cell;

obtaining a sample from the at least one cell;

treating a first fraction of the sample with protease or proteinase;

treating a second fraction of the sample with protease or proteinase;

treating the first fraction of the sample with single-stranded RNase;

treating the second fraction of the sample with double-stranded RNase;

isolating RNA from the first fraction and the second fraction; and preparing a strand specific sequence library.

26. The system of any one or more of embodiments 24-25, wherein obtaining the sample includes lysing the at least one cell to obtain the sample.

27. The system of any one or more of embodiments 22-26 further comprising treating the sample with DNase.

28. The method of any one or more of embodiments 22-27 further comprising treating the sample with protease or proteinase.

29. The method of any one or more of embodiments 22-28 further comprising treating at least one of the first fraction or the second fraction of the sample with protease or proteinase.

30. The system of any one or more of embodiments 22-29, wherein identifying candidate protein binding sites includes identifying protein protected sites; and comparing the protein protected sites with previously published protein data.

31. The system of any one or more of embodiments 23-30 further comprising performing functional analysis of the protein protected sites.

32. The system of embodiment 31, wherein performing functional analysis includes at least one of performing classification and genomic distribution of the protein protected sites; performing conservation analysis of the protein protected sites; or performing SNP association of the protein protected sites.

33. The system of any one or more of embodiments 22-32 further comprising designing RNA probes for the protein protected sites.

34. The system of any one or more of embodiments 22-33 further comprising performing secondary structure analysis of the protein protected sites.

35. The system of any one or more of embodiments 22-34 further comprising comparing the protein protected sites to another set of protein protected sites found in cells under different biological conditions or other cell types to determine the degree of similarity of the protein protected sites to the other set of protein protected sites.

36. The system of any one or more of embodiments 22-35, wherein identifying sequence level motifs includes selecting a site specific candidate protein binding site from the candidate protein binding sites; and performing a MEME motif search on the site specific candidate protein binding site to identify at least one motif.

37. The system of any one or more of embodiments 22-36 further comprising characterizing SNP of the at least one motif.

38. The system of any one or more of embodiments 22-37 further comprising characterizing clustering and cooperativity of the at least one motif.

39. The system of any one or more of embodiments 22-38 further comprising designing RNA probes for the at least one motif.

40. The system of any one or more of embodiments 22-39 further comprising performing secondary structure analysis of the at least one motif.

41. The system of any one or more of embodiments 22-40 further comprising comparing the at least one motif.

42. A system for identifying secondary structures comprising:
  one or more processors configured to execute program instructions;
  a computer-readable medium containing executable instructions that when executed by the one or more processors, cause the computer system to perform the steps of:
    accessing RNase footprinting and control libraries; and
    creating secondary structure profiles from the RNase footprinting and control libraries.

43. The system of embodiment 42, wherein the RNase footprinting library includes a first data set comprising ssRNase treated fractions in the absence of bound protein and a second data set comprising dsRNase treated fractions in the absence of protein.

44. The system of any one or more of embodiments 42-43 further comprising calculating normalized structure scores from the first data set and the second data set.

45. The system of any one or more of embodiments 42-44 further comprising creating base pairing profiles from the normalized structure scores.

46. The system of any one or more of embodiments 42-45 further comprising determining the background distribution of structure scores.

47. The system of any one or more of embodiments 42-46 further comprising determining paired and unpaired nucleotide positions.

48. The system of any one or more of embodiments 42-47 further comprising determining constrained energy-based RNA folding.

49. A method of identifying secondary structures comprising:
  obtaining a first data set comprising ssRNase treated fractions in the absence of bound protein (control library) and a second data set comprising dsRNase treated fractions in the absence of protein (control library);
  calculating normalized structure scores from the first data set and the second data set; and
  creating a secondary structure model from the normalized structure scores.

50. The method of embodiment 49 further comprising creating base pairing profiles from the normalized structure scores.

51. A method of identifying RNA-binding proteins comprising:
  identifying sequence level motifs;
  preparing an RNA substrate having an identified sequence level motif;
  exposing the RNA substrate to a sample containing candidate RNA-binding proteins; and
  isolating candidate RNA binding proteins interacting with the RNA substrate, wherein an isolated candidate RNA binding protein interacting with the RNA substrate is identified as one of the RNA binding proteins.

52. The method of embodiment 51, wherein the step of isolating includes performing an affinity pull-down assay.

53. An isolated nucleic acid molecule comprising, consisting essentially of, or consisting of a sequence having at least 87.5% identity to one selected from the group consisting of Motif 5-AGAAGGCA, Motif 26-TGGTTAGTACTT [SEQ ID NO: 1], Motif 4-ATCTGATC, Motif 7-GATCTCGGAAG [SEQ ID NO: 2], Motif_UTR_4-GAAGCTAAGC [SEQ ID NO: 3], 3' UTR C-rich element-GCCCCCTC-CCCCCCCCCCCC [SEQ ID NO: 4], 3' UTR Unknown element-AGCAGAAG, 3' UTR Unknown hairpin-CAGGC-CGTGCTGCTGCCCA [SEQ ID NO: 5], 5' UTR GGC repeat-GGCGGCGGCGGCGGC [SEQ ID NO: 6], 5' UTR CAG repeat-CGGCAGCAGCAGCAGAAG [SEQ ID NO: 7], 3' UTR TG repeat-TGTGTGTGTGTGTGTGTGTG [SEQ ID NO: 8] 5' UTR Unknown element-AAGATG-GCGGC [SEQ ID NO: 9], CDS AAG repeat-AGAAGAAG, and Intronic Unknown element-CTGTAGAA.

54. The isolated nucleic acid molecule of embodiment 53, wherein the percent identity is 100%.

55. A kit comprising reagents necessary for any method of identifying RNA-protein interaction sites contained herein.

56. The kit of embodiment 55, further comprising the computer system product of any one or more of embodiments 12-41.

57. A kit comprising reagents necessary for any method of identifying RNA secondary structure contained herein.

58. The kit of embodiment 57, further comprising the computer system product of any one or more of embodiments 42-48.

59. A kit comprising reagents necessary for any method of identifying RNA-binding proteins herein.

Further embodiments herein may be formed by supplementing an embodiment with one or more element from any one or more other embodiment herein, and/or substituting one or more element from one embodiment with one or more element from one or more other embodiment herein.

EXAMPLES

The following non-limiting examples are provided to illustrate particular embodiments. The embodiments throughout may be supplemented with one or more detail from one or more example below, and/or one or more element from an embodiment may be substituted with one or more detail from one or more example below.

Example 1

Figure 2A:
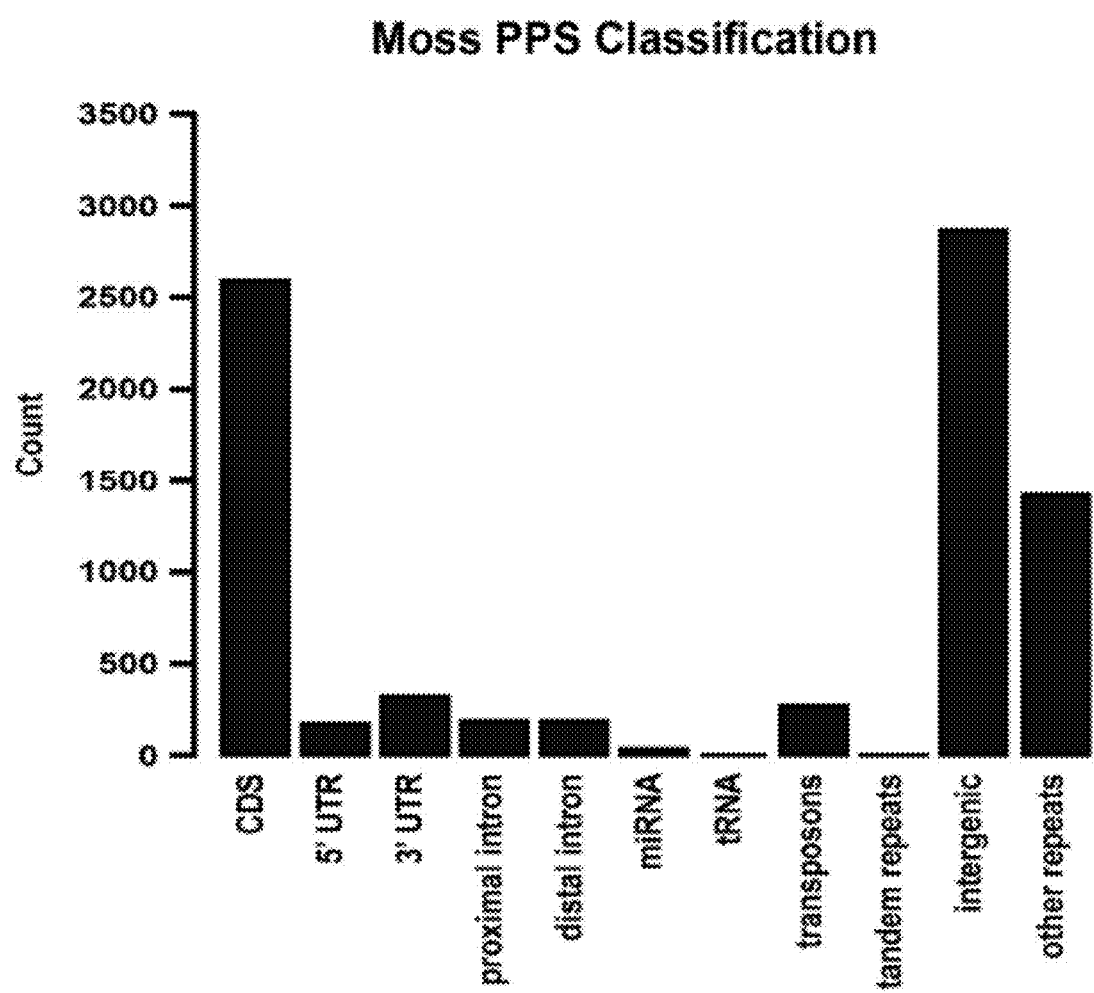
FIGS. 2A-2B illustrate an RNase footprinting approach to identify protein-protected regions of RNA molecules in eukaryotes and contains classification of protein interaction sequences within RNAs from multiple human cell lines and multiple eukaryotic organisms as labeled therein.
Figure 2B:
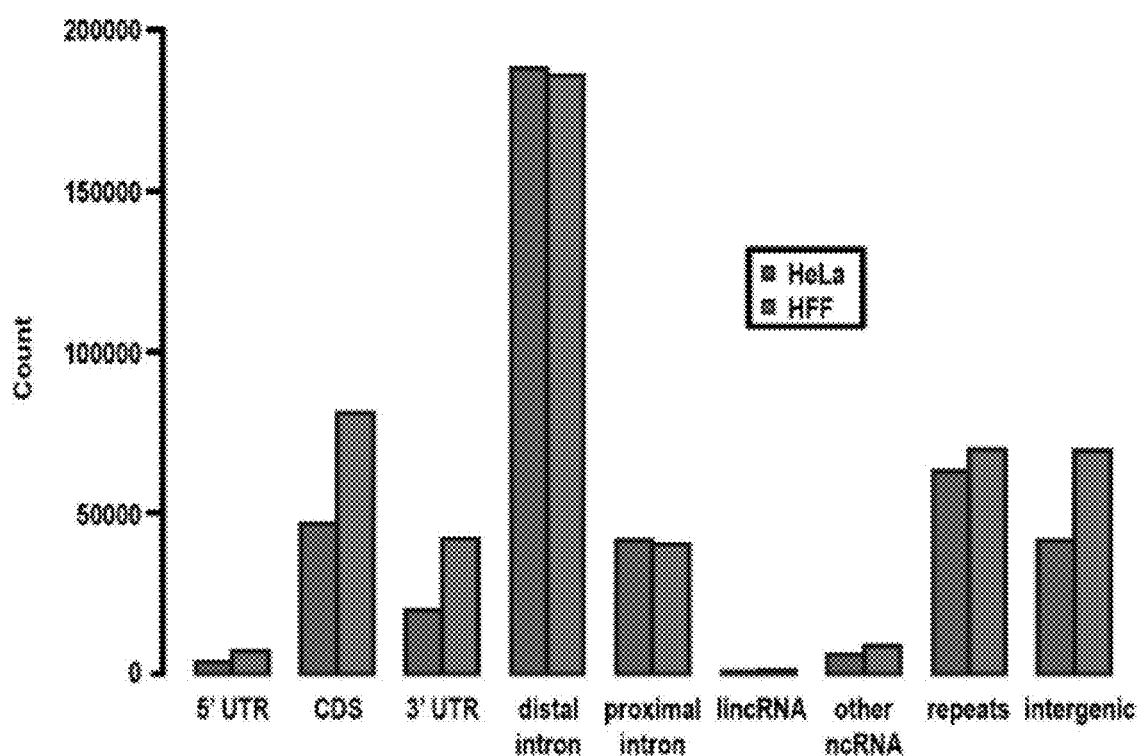
Figure 3:
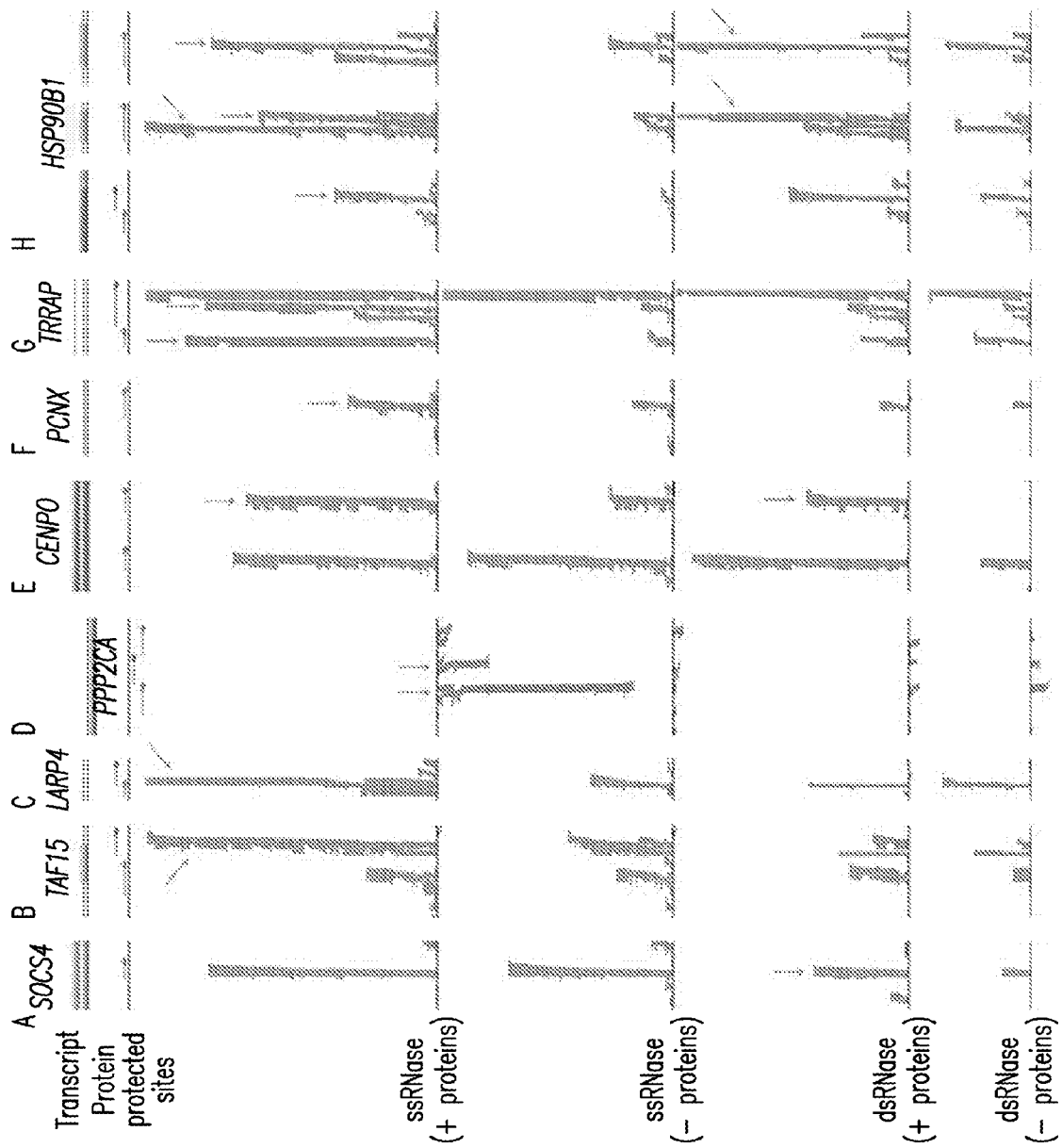
FIGS. 3A-3H illustrate the identification of known RBP binding sites by RNase footprinting.

RNase footprinting analysis performed in HeLa cells using the approach described directly below (FIGS. 1A-1C show a diagram of the approach). Referring to FIGS. 2A-2B, an RNase footprinting approach to identify protein-protected regions of RNA molecules in eukaryotes is illustrated. In FIG. 2A, the graph shows the classification of all moss PPSs that are identified from both ssRNase and dsRNase experiments. In FIG. 2B, the graph shows the classification of all PPSs from two human cell types (HeLa, the left bar in each panel and human foreskin fibroblasts (HFFs), the right bar in each panel), that are identified from both ssRNase and dsRNase experiments.

The PPSs of RNAs are uncovered using a Poisson distribution-based peak finding analysis (FIGS. 2A-2B). This RNase footprinting and analysis approach is used to reliably (FDR=0.05), globally (FIG. 2), and reproducibly (Pearson correlation r=~0.80, FIG. 1C) identify PPSs in the transcriptomes of two human cell types (HeLa and human foreskin fibroblasts (HFFs)), and detected 340,969 and 435,283 total PPSs in HeLa and HFFs respectively (FIG. 2B). This same approach was also used to characterize RNA-protein interaction sites in the Physomitrella patens (moss, a basal plant) transcriptome, and identified 7,685 total PPSs. A statistically significant (p-value→0, hypergeometric test) number of these human PPSs overlapped with previously identified HuR binding sites in both HeLa and HFF cells (Lebedeva et al., 2011; Mukheree et al., 2011, which are incorporated by reference as if fully set forth). Referring to FIGS. 3A-3H, examples of PPSs are illustrated with known RNA-binding protein binding sites identified by RNase footprinting (screenshots from RNase footprinting browser). W and C indicate signal from Watson and Crick strands, respectively. The screen shots also show known binding sites for HuR in SOCS4 (A), TAF 15 protein in TAF15 mRNA (B), PTB in LARP4 (C), PUM2 in PPP2CA (D), EWRS1 in CENPD (E), FUS in PCNX (F), QKI in TRRAP (G), and SRFS1 in HSP90B1 (H). Arrows designate the known RNA-binding protein sites overlapping the identified PPSs. These results indicate the RNase footprinting approaches are reliably identifying protein-bound regions of eukaryotic mRNAs.

The majority of PPSs in the human cell lines were located within human mRNAs, with introns demonstrating enrichment compared to exonic regions (FIG. 2B). Interestingly, more PPSs were localized in the 3' compared to the 5' UTR in moss as well as both human cell lines, which is consistent with the role of the 3' UTR in post-transcriptional regulation in eukaryotes (FIGS. 2A-2B). Numerous PPSs in repetitive element-derived and intergenic (unannotated) transcripts were also observed (FIGS. 2A-2B) in both organisms. The unannotated (intergenic) RNAs in both humans and plants with high levels of PPSs will be of significant interest for future study, as these are likely unannotated coding and non-coding transcripts in these transcriptome that interact with specific RBPs. It is also worth noting that PPSs were identified in other biologically important classes of RNA, including lnc- and sncRNAs (FIGS. 2A-2B). Within these classes of RNAs, TERC (the RNA subunit of telomerase) was significantly protein-bound, which was expected given that this ncRNA is known to interact with the RBP Tert. In total, the data produced by our RNase footprinting approach provides a global view of RNA-protein interactions within the human transcriptome.

Based on these preliminary results and our previous studies (Li et al., 2012, Zheng et al., 2010, which are incorporated herein by reference as if fully set forth), these approaches can be used to determine protein-protected regions of RNAs.

Finally, to identify over-represented motifs within the protein-protected RNA regions, the PPSs found specifically in the 5' UTR, protein-coding region, and 3' UTR were used as datasets to perform a motif search using MEME (meme.sdsc.edu/meme/). This analysis identified >100 motifs within these specific transcript regions, many of which have been previously identified as RBP interacting sequences.

Figure 4A:
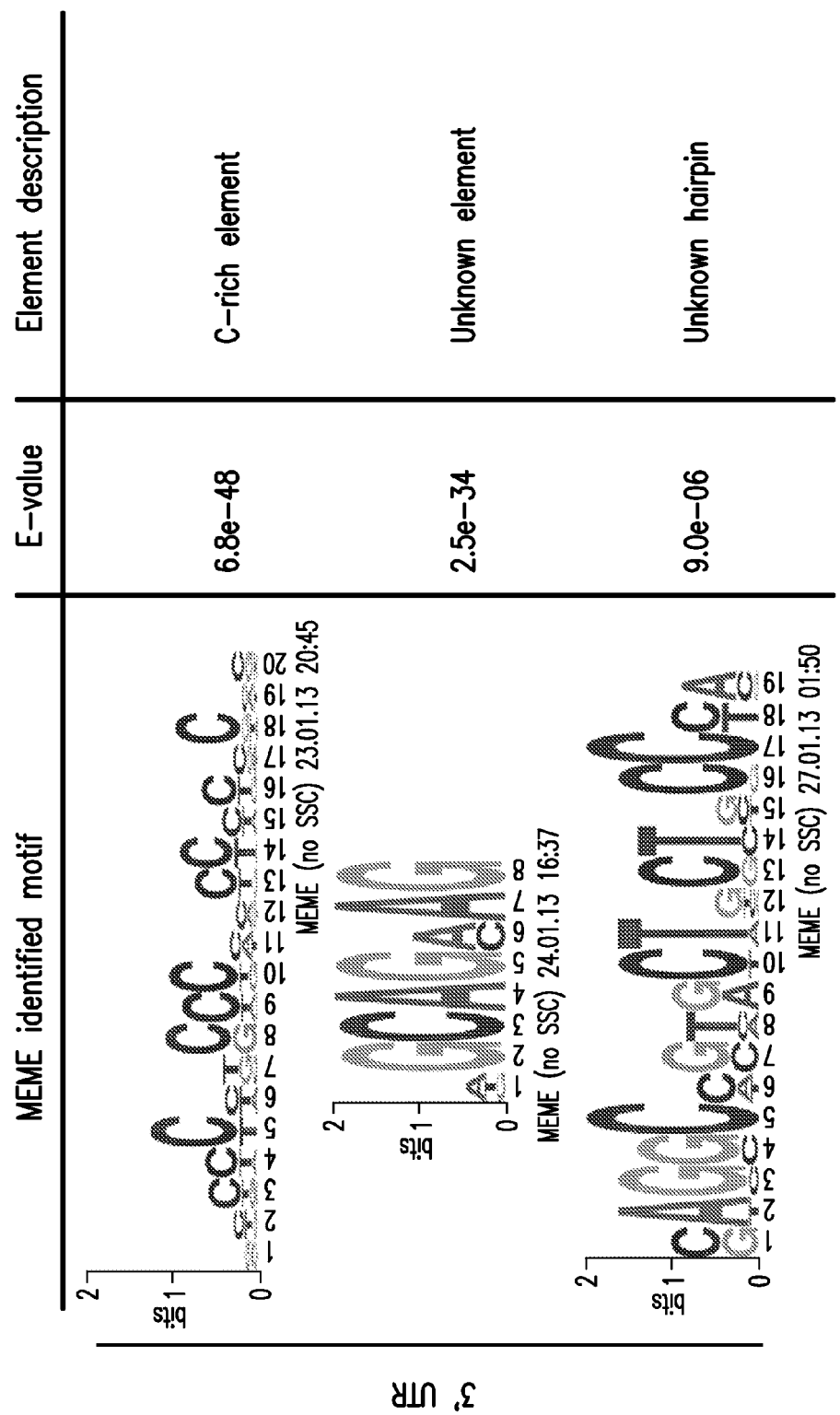
FIGS. 4A-4B illustrate the identification of specific motifs for RNA-protein interaction by RNase footprinting, and the subsequent identification of the interacting protein(s).
Figure 4A:
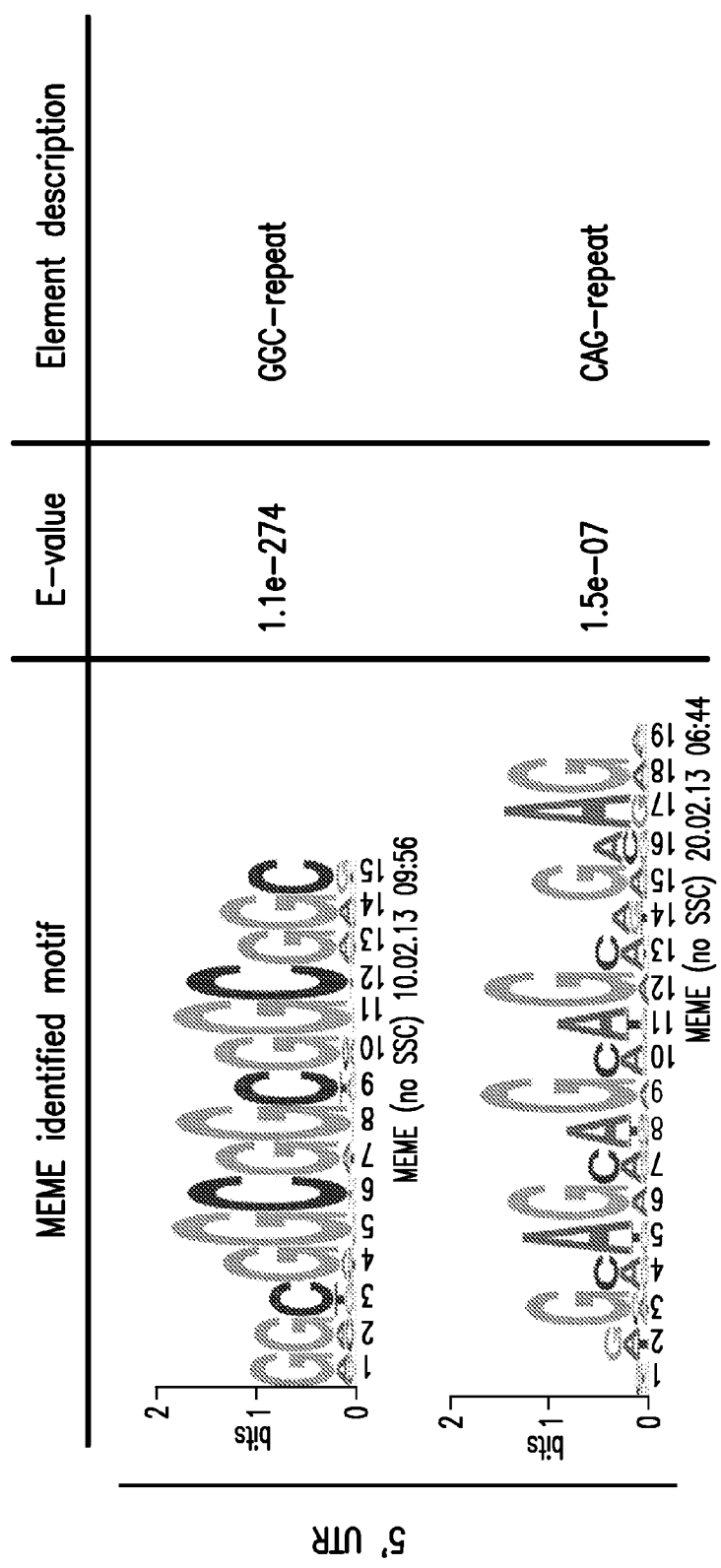
Figure 4B:
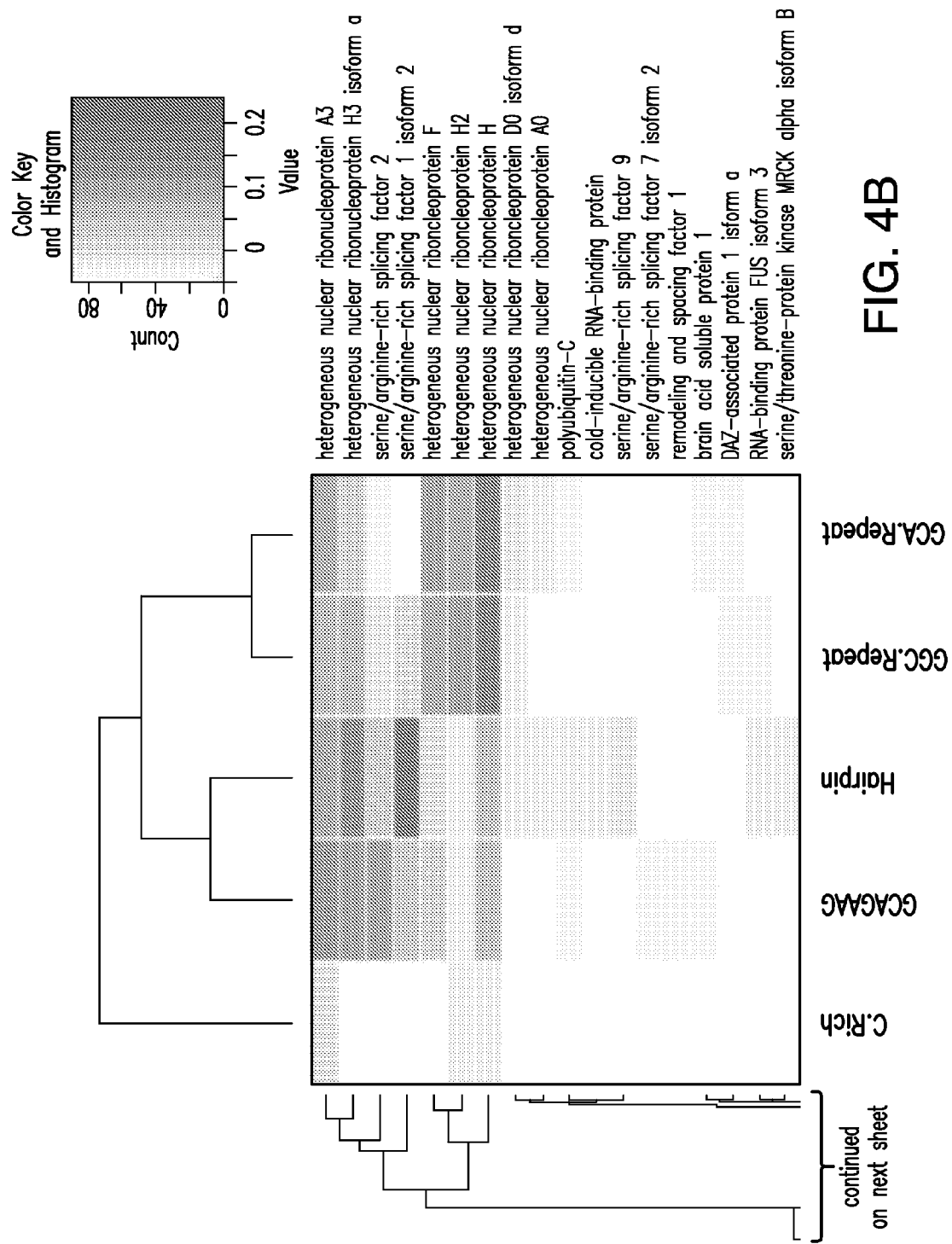
Figure 4B:
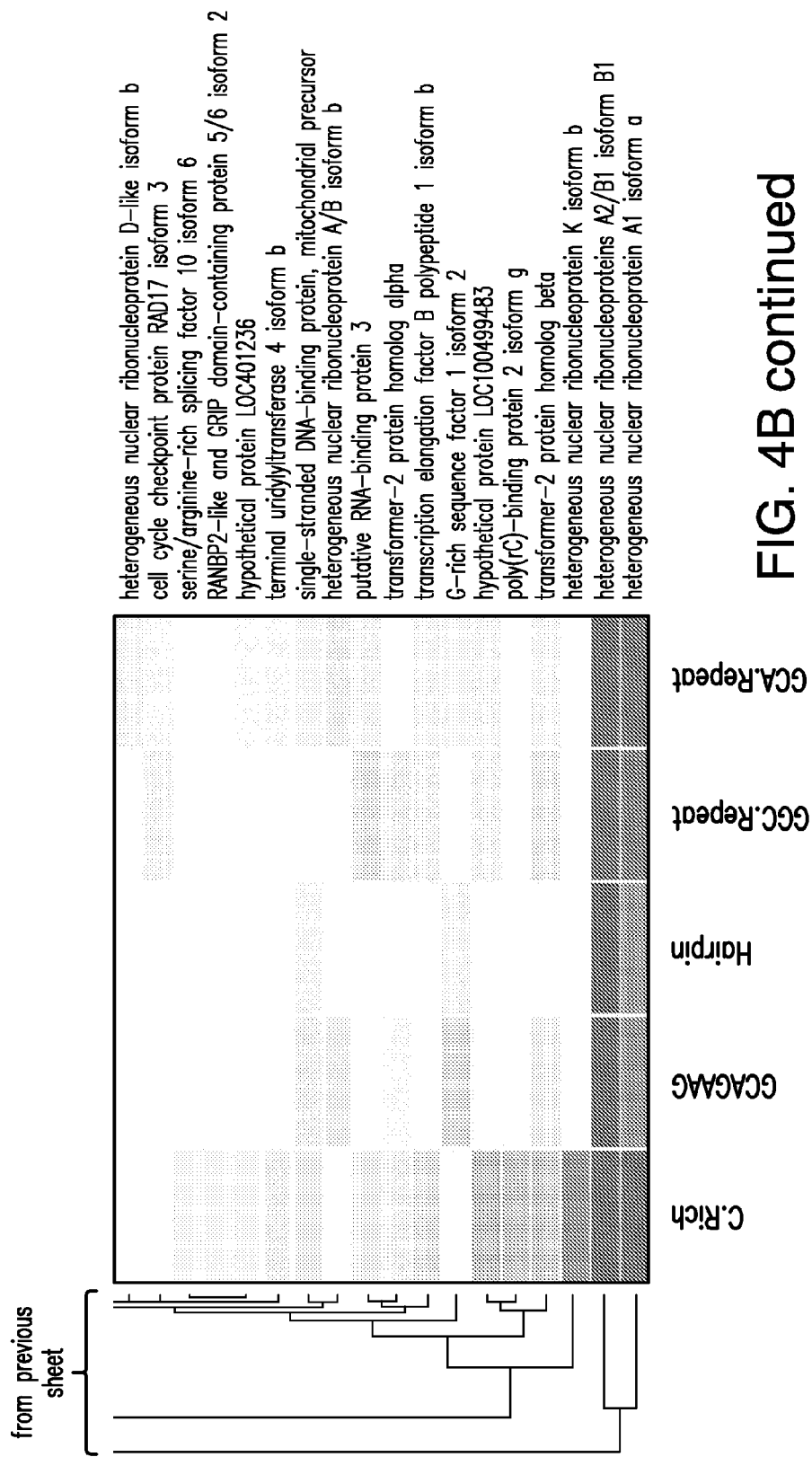

Referring to FIGS. 4A-4B, over-represented sequence motifs identified by MEME analysis of PPS sequences from the 3' UTR of transcripts from HeLa cells are shown. Examples of over-represented motifs, both novel and highly similar to known RBP-binding motifs (e.g αCP2 is known to bind a C-rich sequence) identified using PPSs from the 3' UTRs of HeLa transcripts are in FIG. 4A. Sequences illustrated in FIG. 4A are reproduced in Table 1, below. RNase-assisted RNA-affinity chromatography using the motif from FIG. 4A identified by MEME-based analysis of PPS sequences from the 3' UTR of transcripts from HeLa cells uncovers specific RNA-binding proteins interacting with each sequence motif. These results demonstrate that we are identifying bona fide RNA-binding protein interacting sequences, a number of which have not been previously uncovered.

TABLE 1

| Sequence | SEQ ID NO | Location (3' UTR or 5' UTR) | Element description |
|---|---|---|---|
| GCCCCCTCCCCCCCCCCCC* | 4 | 3' UTR | C-rich element |
| AGCAGAAG | | 3' UTR | Unknown element |
| CAGGCCGTGCTGCTGCCA* | 5 | 3' UTR | Unknown hairpin |
| GGCGGCGGCGGCGGC* | 6 | 5' UTR | GGC repeat |
| CGGCAGCAGCAGCAGAAG* | 7 | 5' UTR | CAG repeat |

A number of novel protein interacting sites that are highly prevalent in human mRNAs were uncovered, a number of which are depicted in FIG. 4A and shown by asterisk in Table 1. Overall, the RNase footprinting approach identifies known and novel RNA-binding protein interaction sites in human mRNAs (FIGS. 3A-3H and 4A-4B), and can be used as a new approach for identifying previously uncharacterized RBPs in any eukaryotic organism of interest.

REFERENCES

[1] Cooper, T. A., Wan, L., and Dreyfiss, G. (2009). RNA and disease. Cell 136, 777-793.
[2] Dreyfuss, G., Matunis, M. J., Pinol-Roma, S., and Burd, C. G. (1993). hhRNP proteins and the biogenesis of mRNA. Annu Rev Biochem 62, 289-321.

[3] Glisovic, T., Bachorik, J. L., Young, J., and Dreyfuss, G. (2008). RNA-binding proteins and post-transcriptional gene regulation. FEBS Lett 582, 1977-1986.
[4] Keene, J. D. (2001). Ribonucleoprotein infrastructure regulating the flow of genetic information between the genome and the proteome. Proc Natl Acad Sci USA 98, 7018-7024.
[5] Lebedeva, S., Jens, M., Theil, K., Schwanhausser, B., Selbach, M., Landthaler, M., Rajewsky, N. (2011). Transcriptome-wide analysis of regulatory interactions of the RNA-binding protein HuR. Mol Cell 43, 340-352.
[6] Li, F., Zheng, Q., Ryvkin, P., Dragomir, I., Desai, Y., Aiyer, S., Valladares, O., Yang, J., Bambina, S., Sabin, L. R., et al. (2012). Global analysis of RNA secondary structure in two metazoans. Cell Reports In press.
[7] Lukong, K. E., Chang, K. W., Khandijian, E. W., and Richard, S. (2008). RNA-binding proteins in human genetic disease. Trends Genet 24, 416-425.
[8] Mukherjee, N., Corcoran, D. L., Nusbaum, J. D., Reid, D. W., Georgiev, S., Hafner, M., Ascano, M., Jr., Tuschl, T., Ohler, U., and Keene, J. D. (2011). Integrative regulatory mapping indicates that the RNA-binding protein HuR couples pre-mRNA processing and mRNA stability. Mol Cell 43, 327-339.
[9] Wang, G. S., and Cooper, T. A. (2007). Splicing in disease: disruption of the splicing code and the decoding machinery. Nat Rev Genet 8, 749-761.
[10] Zheng, Q., Ryvkin, P., Li, F., Dragomir, I., Valladares, 0., Yang, J., Cao, K., Wang, L. S., and Gregory, B. D. (2010). Genome-Wide Double-Stranded RNA Sequencing Reveals the Functional Significance of Base-Paired RNAs in Arabidopsis. PLoS Genet 6, e1001141.

The references cited throughout this application are incorporated for all purposes apparent herein and in the references themselves as if each reference was fully set forth. For the sake of presentation, specific ones of these references are cited at particular locations herein. A citation of a reference at a particular location indicates a manner(s) in which the teachings of the reference are incorporated. However, a citation of a reference at a particular location does not limit the manner in which all of the teachings of the cited reference are incorporated for all purposes.

It is understood, therefore, that this invention is not limited to the particular embodiments disclosed, but is intended to cover all modifications which are within the spirit and scope of the invention as defined by the appended claims; the above description; and/or shown in the attached drawings.

What is claimed is:

1. A method of transcriptome-wide identification of RNA-protein interaction sites, comprising:
   (a) preparing an RNase footprinting library, wherein said preparation comprises:
      i. exposing a eukaryotic cell to a crosslinking agent;
      ii. obtaining a nucleic acid-containing sample from the cell;
      iii. treating a first fraction of the sample with a single-stranded RNase;
      iv. thereafter treating the first fraction with a protease or proteinase;
      v. treating a second fraction of the sample with a double-stranded RNase;
      vi. thereafter treating the second fraction with a protease or proteinase;
      vii. isolating RNA from the first fraction and the second fraction; and
      viii. preparing a strand specific sequence library from the isolated RNA;
   (b) preparing an RNase control library, wherein said preparation comprises:
      i. exposing a eukaryotic cell to a crosslinking agent;
      ii. obtaining a nucleic acid-containing sample from the cell;
      iii. treating a first fraction of the sample with protease or proteinase;
      iv. thereafter treating the first fraction of the sample with a single-stranded RNase;
      v. treating a second fraction of the sample with protease or proteinase;
      vi. thereafter treating the second fraction of the sample with a double-stranded RNase;
      vii. isolating RNA from the first fraction and the second fraction; and
      viii. preparing a strand specific sequence library from the isolated RNA,
   (c) identifying candidate protein binding sites within the RNase footprinting library; and
   (d) identifying sequence level motifs within the candidate protein binding sites.

2. The method of claim 1, wherein the sample is obtained by lysing the cell.

3. The method of claim 2, further comprising treating the sample with a DNase following cell lysis.

4. The method of claim 1, wherein identifying candidate protein binding sites comprises identifying protein protected sites; and comparing the protein protected sites with previously published protein data.

5. The method of claim 1, wherein identifying sequence level motifs comprises selecting a site specific candidate protein binding site from the candidate protein binding sites; and using a motif finding algorithm to identify at least one motif from the site specific candidate protein binding site.

6. The method of claim 5, wherein the site specific candidate binding site is found in the 5' UTR, the protein coding region, or the 3' UTR.

7. The method of claim 5, further comprising validating the motif by performing a competitive pull-down assay.

* * * * *

SEQUENCE LISTING

```
<160> NUMBER OF SEQ ID NOS: 9

<210> SEQ ID NO 1
<211> LENGTH: 12
<212> TYPE: DNA
<213> ORGANISM: Homo sapiens

<400> SEQUENCE: 1
tggttagtac tt                                                          12

<210> SEQ ID NO 2
<211> LENGTH: 11
<212> TYPE: DNA
<213> ORGANISM: Homo sapiens

<400> SEQUENCE: 2
gatctcggaa g                                                           11

<210> SEQ ID NO 3
<211> LENGTH: 10
<212> TYPE: DNA
<213> ORGANISM: Homo sapiens

<400> SEQUENCE: 3
gaagctaagc                                                             10

<210> SEQ ID NO 4
<211> LENGTH: 20
<212> TYPE: DNA
<213> ORGANISM: Homo sapiens

<400> SEQUENCE: 4 gcccctccc cccccccccc                                                   20

<210> SEQ ID NO 5
<211> LENGTH: 19
<212> TYPE: DNA
<213> ORGANISM: Homo sapiens
```

```
<400> SEQUENCE: 5
caggccgtgc tgctgccca                                                19

<210> SEQ ID NO 6
<211> LENGTH: 15
<212> TYPE: DNA
<213> ORGANISM: Homo sapiens

<400> SEQUENCE: 6
ggcggcggcg gcggc                                                    15

<210> SEQ ID NO 7
<211> LENGTH: 18
<212> TYPE: DNA
<213> ORGANISM: Homo sapiens

<400> SEQUENCE: 7
cggcagcagc agcagaag                                                 18

<210> SEQ ID NO 8
<211> LENGTH: 20
<212> TYPE: DNA
<213> ORGANISM: Homo sapiens

<400> SEQUENCE: 8
tgtgtgtgtg tgtgtgtgtg                                               20

<210> SEQ ID NO 9
<211> LENGTH: 11
<212> TYPE: DNA
<213> ORGANISM: Homo sapiens

<400> SEQUENCE: 9
aagatggcgg c                                                        11
```